(12) United States Patent
Selvitelli

(10) Patent No.: US 9,289,272 B2
(45) Date of Patent: Mar. 22, 2016

(54) ANESTHETIC SYRINGE

(75) Inventor: David M. Selvitelli, Suffield, CT (US)

(73) Assignee: Covidien LP, Mansfield, MA (US)

( * ) Notice: Subject to any disclaimer, the term of this patent is extended or adjusted under 35 U.S.C. 154(b) by 630 days.

(21) Appl. No.: 13/438,853

(22) Filed: Apr. 4, 2012

(65) Prior Publication Data

US 2012/0258421 A1 Oct. 11, 2012

Related U.S. Application Data

(60) Provisional application No. 61/471,903, filed on Apr. 5, 2011.

(51) Int. Cl.
*A61C 19/08* (2006.01)
*A61C 5/06* (2006.01)
(Continued)

(52) U.S. Cl.
CPC .................. *A61C 5/062* (2013.01); *A61M 5/19* (2013.01); *A61M 5/24* (2013.01); *A61M 5/3137* (2013.01); *A61M 5/3129* (2013.01); *A61M 5/3134* (2013.01); *A61M 5/3148* (2013.01); *A61M 5/31511* (2013.01); *A61M 5/3205* (2013.01); *A61M 5/3216* (2013.01); *A61M 5/3243* (2013.01); *A61M 5/3286* (2013.01); *A61M 5/3291* (2013.01); *A61M 5/3298* (2013.01); *A61M 5/34* (2013.01); *A61M 5/344* (2013.01);
(Continued)

(58) Field of Classification Search
CPC . A61M 5/24; A61M 5/31511; A61M 5/3137; A61M 2005/247; A61M 5/3202; A61M 5/3243

USPC ......... 604/232, 227, 201, 192, 200, 218, 234, 604/117, 240, 120, 164.01, 164.08, 195, 604/196, 197, 198
See application file for complete search history.

(56) References Cited

U.S. PATENT DOCUMENTS 1,234,582 A * 7/1917 Trueblood .................... 604/191
1,798,117 A * 3/1931 Brockway .................... 604/232
(Continued)

FOREIGN PATENT DOCUMENTS

EP 0139872 A1 5/1985
EP 2058020 A2 5/2009
(Continued)

OTHER PUBLICATIONS

Exam Report issued Sep. 20, 2012 in corresponding Australian Patent Application No. 2012201968, 4 pages.
(Continued)

*Primary Examiner* — Kevin C Sirmons
*Assistant Examiner* — William Carpenter
(74) *Attorney, Agent, or Firm* — Lisa E. Winsor, Esq.

(57) ABSTRACT

A syringe assembly for dispensing medicine from a cartridge having a diaphragm and a piston opposite the diaphragm. The assembly includes a barrel having a hollow interior, an open proximal end, a closed distal end, and an outlet. The assembly also includes a cartridge receiver slidably receivable in the hollow interior of the barrel. The receiver includes an interior space for receiving the cartridge, an access needle extending into the interior space for puncturing the diaphragm of the cartridge. The access needle directs fluid to the barrel outlet. The cartridge receiver includes a plunger rod movable into the interior space of the cartridge receiver for engaging the piston of the cartridge to selectively force medicine in the cartridge through the access needle.

15 Claims, 19 Drawing Sheets

(51) Int. Cl.

| | | |
|---|---|---|
| *A61M 5/19* | (2006.01) | |
| *A61M 5/24* | (2006.01) | |
| A61M 5/31 | (2006.01) | |
| A61M 5/315 | (2006.01) | |
| A61M 5/32 | (2006.01) | |
| A61M 5/34 | (2006.01) | |
| A61M 5/48 | (2006.01) | |

(52) U.S. Cl.
CPC ............... *A61M 5/484* (2013.01); *A61M 5/488* (2013.01); *A61M 2005/247* (2013.01); *A61M 2005/31598* (2013.01); *A61M 2005/3267* (2013.01); *A61M 2005/341* (2013.01); *A61M 2205/586* (2013.01); *A61M 2205/587* (2013.01); *A61M 2205/59* (2013.01)

(56) References Cited

U.S. PATENT DOCUMENTS

| | | | | |
|---|---|---|---|---|
| 2,939,459 | A * | 6/1960 | Lazarte et al. | 604/191 |
| 3,074,541 | A * | 1/1963 | Roehr | 206/229 |
| 3,110,309 | A * | 11/1963 | Higgins | 604/201 |
| 3,316,909 | A * | 5/1967 | Cowley | A61M 5/31 604/227 |
| 3,380,450 | A * | 4/1968 | Adelberger | A61M 5/28 604/117 |
| 3,785,379 | A * | 1/1974 | Cohen | 604/88 |
| 3,811,441 | A * | 5/1974 | Sarnoff | 604/201 |
| 3,939,833 | A | 2/1976 | Hansson et al. | |
| 4,109,653 | A | 8/1978 | Kozam et al. | |
| 4,171,698 | A * | 10/1979 | Genese | 604/88 |
| 4,820,275 | A | 4/1989 | Haber et al. | |
| 4,861,335 | A * | 8/1989 | Reynolds | A61M 5/2448 604/191 |
| 5,281,198 | A * | 1/1994 | Haber et al. | 604/86 |
| 5,476,449 | A * | 12/1995 | Richmond | 604/87 |
| 5,542,934 | A * | 8/1996 | Silver | 604/191 |
| 5,785,682 | A * | 7/1998 | Grabenkort | A61M 5/284 604/191 |
| 5,848,996 | A | 12/1998 | Eldor | |
| 5,902,278 | A * | 5/1999 | Aguilar | A61M 5/3135 604/187 |
| 6,086,569 | A | 7/2000 | Schweizer | |
| 6,458,101 | B1 | 10/2002 | Hu | |
| 6,595,978 | B2 * | 7/2003 | Granier | A61M 5/24 600/578 |
| 7,951,108 | B2 * | 5/2011 | Harper et al. | 604/82 |
| 8,529,517 | B2 * | 9/2013 | Lee | A61M 5/31596 604/191 |
| 2002/0147430 | A1 | 10/2002 | Collins et al. | |
| 2005/0004518 | A1 * | 1/2005 | Call | A61M 25/1018 604/97.02 |
| 2007/0060897 | A1 | 3/2007 | Wang | |
| 2008/0051729 | A1 | 2/2008 | Cheng | |

FOREIGN PATENT DOCUMENTS

| | | |
|---|---|---|
| JP | 54-033390 A | 3/1979 |
| JP | 6-7746 U | 2/1994 |
| JP | 9-511153 A | 11/1997 |
| JP | 11-502731 A | 3/1999 |
| JP | 2007-526023 A | 9/2007 |
| JP | 2008-161673 A | 7/2008 |
| WO | 95/13842 A1 | 5/1995 |
| WO | 01/00261 A1 | 1/2001 |

OTHER PUBLICATIONS

Notice of Reasons for Rejection mailed May 14, 2013 in corresponding Japanese Patent Application No. 2012-085741, 3 pages.
Extended European Search Report in European Application No. 12162966.1, dated Aug. 28, 2014.
Exam Report issued in corresponding Canadian Application No. 2,773,271 dated Jul. 17, 2014, 2 pages.
Notice of Reasons for Rejection issued in Japanese Patent Application No. 2014-117405, mailed Apr. 24, 2015.

* cited by examiner

ANESTHETIC SYRINGE

CROSS REFERENCE TO RELATED APPLICATION

This application claims priority to U.S. Patent Application 61/471,903 filed Apr. 5, 2011, which is hereby incorporated by reference in its entirety.

BACKGROUND

The present invention generally relates to devices for injecting liquid medications from prefilled cartridges and more particularly to single use disposable syringe assemblies for injecting local anesthetics.

Many dental procedures use anesthetic to numb an area of a patient's mouth to reduce pain and discomfort a patient may feel. Conventionally, a re-usable breech-loading, metallic, cartridge-type syringe assembly is used to inject the anesthetic. The dental syringe assembly includes a syringe, a cartridge, and a needle. The syringe may be constructed of chrome-plated brass and stainless steel and may include a needle adapter, a syringe barrel, a plunger rod, a finger grip, and a thumb ring. Typically, the syringe must be sterilized before each use.

Generally, the cartridge or carpule is a vial containing a local anesthetic among other ingredients. The cartridge may include a glass cylinder, a piston, and a rubber diaphragm held in position by an aluminum band. The cartridge is usually wiped with alcohol prior to being loaded into the syringe.

The needle of the dental syringe permits local anesthetic to travel from the dental cartridge into tissue surrounding the needle tip. Needles may be pre-sterilized and disposable. The needle may consist of a single piece of metal tubing surrounded by a plastic or a metal needle hub attached to the needle adapter of the syringe.

Assembly of a dental syringe often requires removing a sterilized syringe from its container and placing an alcohol wiped cartridge into the syringe with the plunger rod of the syringe fully retracted. The rubber diaphragm on a distal end of the cartridge is inserted into the syringe first and the plunger rod engages the piston positioned at a proximal end of the cartridge. The syringe includes an access needle for puncturing the cartridge. As the plunger rod advances, anesthetic is forced out of the cartridge toward a need assembly. The needle assembly including a needle and protective cap may be secured to the syringe. The protective cap is removed from the needle and the syringe is ready for use.

After the assembled dental syringe is used, the needle assembly must be recapped, disconnected from the syringe and disposed in a sharps container, and the cartridge must be removed and disposed in a biohazard bag or sharps container. Thereafter, the syringe may be sterilized for its next use.

SUMMARY

In one aspect, the present invention includes a syringe assembly for dispensing medicine from a cartridge having a diaphragm and a piston opposite the diaphragm. The assembly comprises a barrel having a hollow interior, an open proximal end extending into the hollow interior, a closed distal end opposite the proximal end, and an outlet adapted for fluid communication with a delivery needle for delivering medicine to tissue of a subject. The assembly also includes a cartridge receiver slidably receivable in the hollow interior of the barrel. The cartridge receiver includes an interior space sized and shaped for receiving the cartridge, an access needle extending into the interior space of the cartridge receiver for puncturing the diaphragm of the cartridge received in the interior space to access medicine. The access needle directs fluid to the barrel outlet when the cartridge receiver is received in the hollow interior of the barrel. The cartridge receiver further comprises a plunger rod movable into the interior space of the cartridge receiver for engaging the piston of the cartridge received in the receiver to selectively force medicine in the cartridge through the access needle.

Other aspects of the present invention will be apparent in view of the following description and claims.

BRIEF DESCRIPTION OF THE DRAWINGS

Corresponding reference characters indicate corresponding parts throughout the drawings.

DETAILED DESCRIPTION OF THE DRAWINGS

Figure 1A:
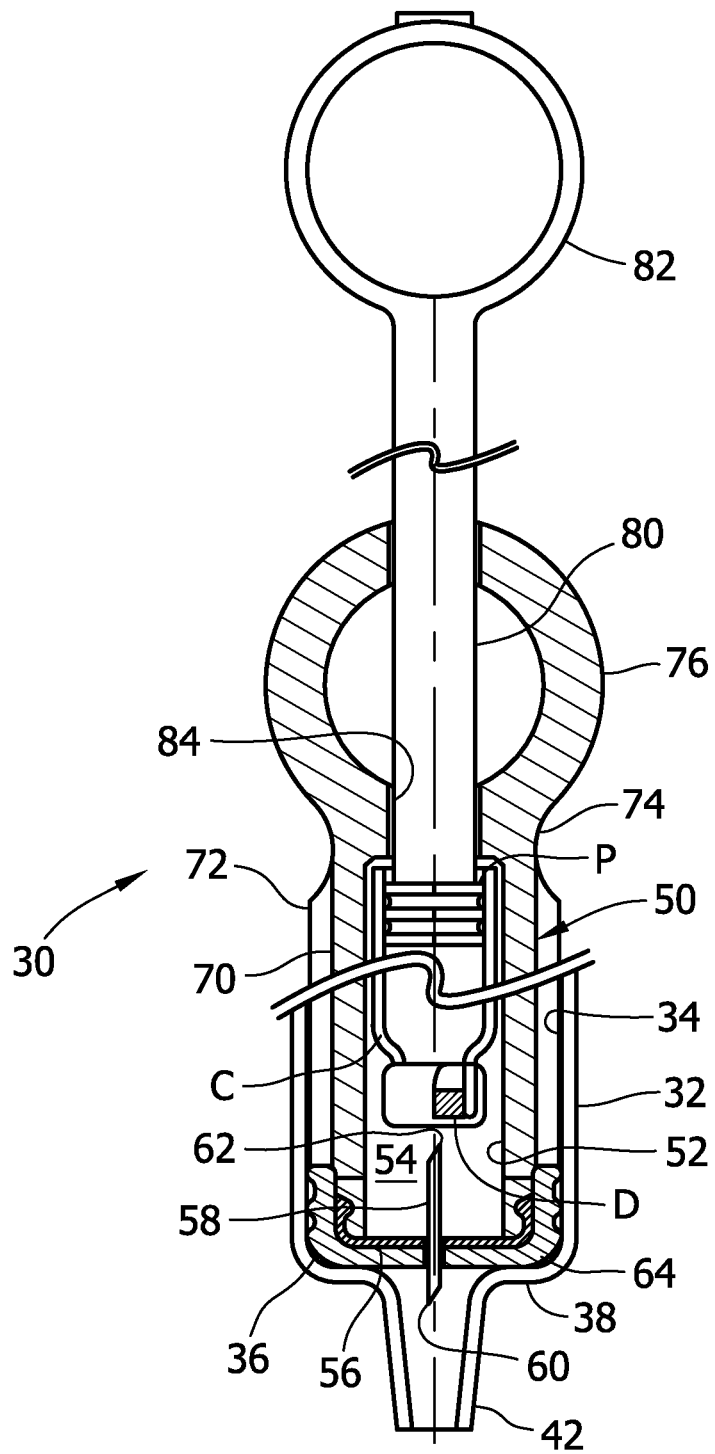
FIG. 1a is a side elevation in partial section of a syringe assembly of a first embodiment of the present invention shown in a first position.

Referring to FIG. 1a, a syringe assembly of a first embodiment is designated in its entirety by the reference number 30. The syringe assembly 30 includes a barrel 32 having an inner wall 34 defining a hollow interior 36 having a closed distal end 38 and an open proximal end (not shown) opposite the closed end. An outlet 42 is provided in the closed end 38 of the barrel 32. A conventional deliver needle may be attached to the outlet 42.

In addition, the syringe assembly 30 includes a cartridge receiver, generally designated by 50, slidably received in the barrel 32. The cartridge receiver 50 includes an interior wall 52 defining a interior space 54 sized and shaped for receiving a conventional cartridge C containing medicine (e.g., anesthetic). The cartridge receiver 50 includes a removable distal cap or cover 56 having an access needle 58. The access needle 58 includes a distal delivery point 60 and a sharp proximal access point 62 adapted to penetrate a diaphragm D of the cartridge C. An elastomeric seal 64 surrounds the cap 56 for sealingly engaging the inner wall 34 of the barrel 32. An outer surface 70 of the cartridge receiver 50 includes spaced ribs 72 for guiding the receiver as it reciprocates in the barrel 32. A proximal end of the receiver 50 includes scalloped sides 74 for receiving fingers of the user. Further, the proximal end of the receiver 50 includes an outer thumb ring 76 that is used when the syringe assembly 30 is readied for injection as will be explained in detail below.

Figure 1B:
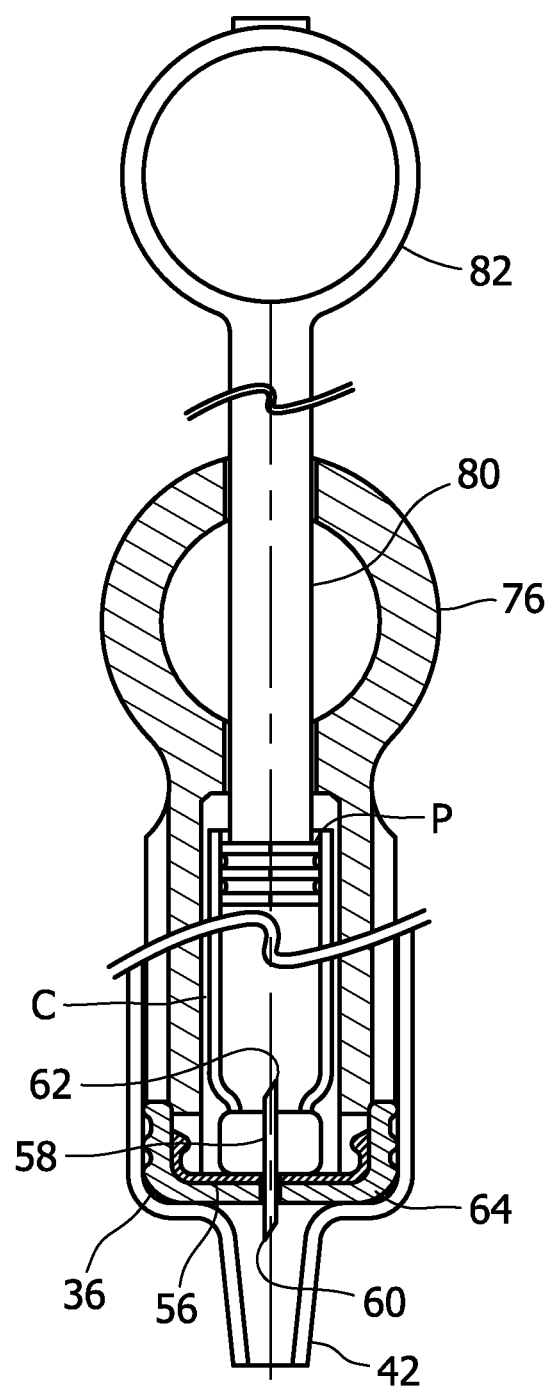
FIG. 1b is a side elevation in partial section of the syringe assembly of FIG. 1a shown in a second position.
Figure 1C:
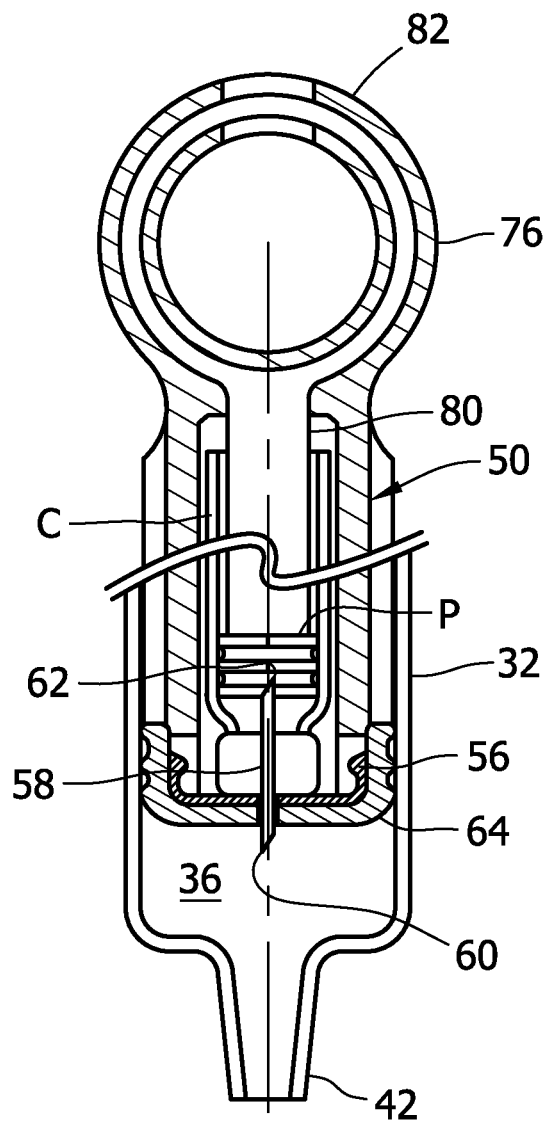
FIG. 1c is a side elevation in partial section of the syringe assembly of FIG. 1a shown in a third position.

A plunger rod 80 extends inside the cartridge receiver and engages a piston P on the cartridge C. A proximal end of the plunger rod 80 includes a thumb ring 82. The plunger rod 80 extends through an opening 84 in the thumb ring 76 of the cartridge receiver 50. As shown in FIG. 1b, a user prepares the cartridge C for use by pushing the plunger rod 80 distally to engage the access tip 60 of the access needle 58 with the diaphragm D of the cartridge C. Once in this position, the cartridge receiver 50 may be drawn proximally relative to the plunger rod 80 until the thumb rings 82, 76 of the plunger rod 80 and cartridge receiver 50, respectively, overlap (e.g., concentrically aligned as shown in FIG. 1c). This action drives the piston P distally in the cartridge C, forcing medicine through the access needle 58 and into the hollow interior 36 of the barrel 32. Once in this position, the cartridge receiver 50 and plunger rod 80 are moved together in a distal direction to eject the medicine from the barrel 32 through the outlet 42 and into a delivery needle (not shown).

Figure 2:
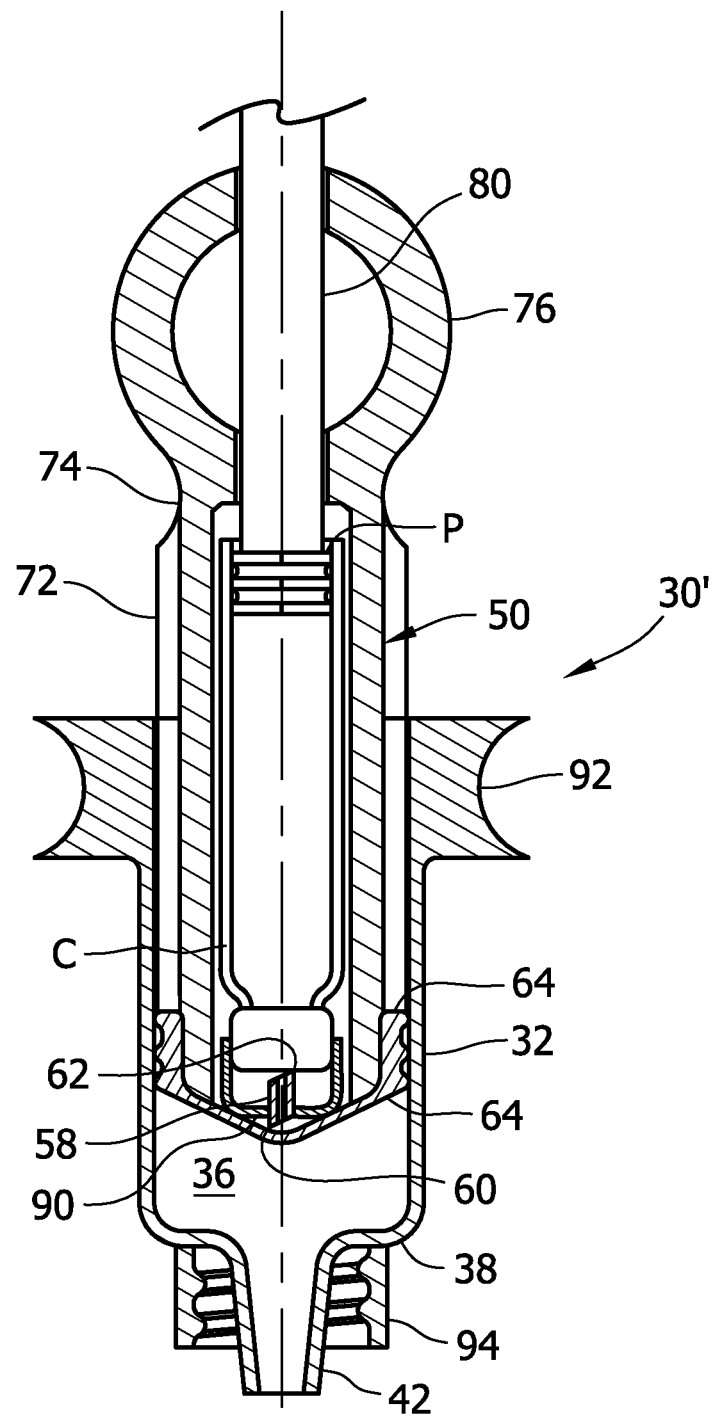
FIG. 2 is a side elevation in partial section of the syringe assembly of a second embodiment.

A second embodiment of a syringe assembly 30' of the present invention is shown in FIG. 2. Rather than having a separate cap 56, the cartridge receiver 50 has a unitary cap and seal 64. Further, an access adapter 90 having an access needle 58 is positioned on the cartridge C. The barrel 32 is provided with a finger flange 92 and a luer lock tip 94. Because other physical characteristics of this embodiment are similar to those previously described, they will not be described in further detail.

Figure 3:
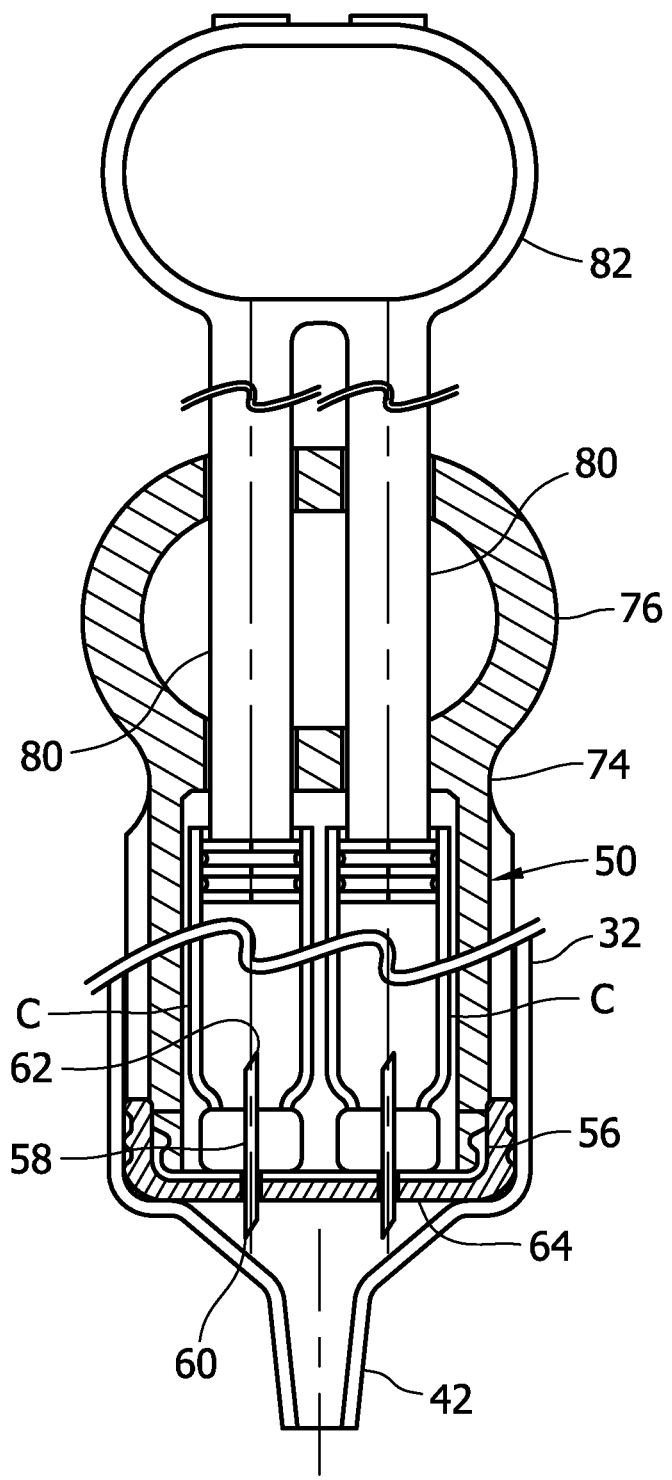
FIG. 3 is a side elevation in partial section of the syringe assembly of a third and fourth embodiment.
Figure 4A:
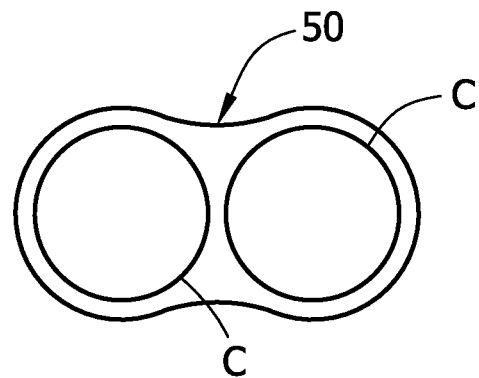
FIGS. 4a and 4b are schematic cross sections of the assemblies of the third and fourth embodiments.
Figure 4B:
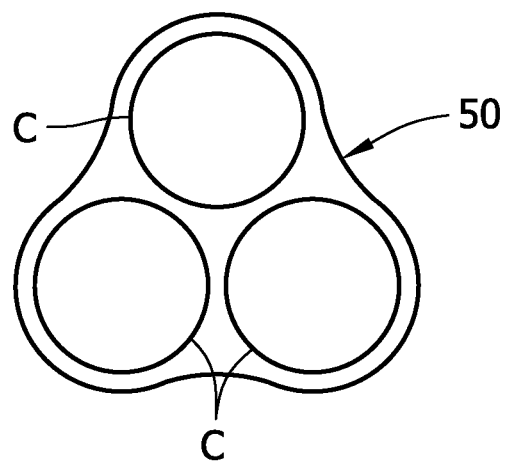

In a third embodiment of the present invention shown in FIG. 3, the cartridge receiver 50 is adapted for receiving two cartridges C simultaneously. Further, the third embodiment has two rods 80. Other features of the third embodiment are similar to those of the first embodiment described above and will not be described in further detail. A schematic cross section of the syringe assembly of the third embodiment is shown in FIG. 4a. As will be appreciated by those skilled in the art, the cartridge receiver 50 may be adapted to receive three cartridges C as shown in a schematic cross section of the syringe assembly of a fourth embodiment shown in FIG. 4b. This embodiment includes three access needles (not shown) extending through the cap of the receiver and three plunger rods (not shown) adapted to engage the respective seals of the cartridges C. Those skilled in the art will appreciate that still other embodiments adapted for receiving still more cartridges are also within the scope of the present invention.

Figure 5:
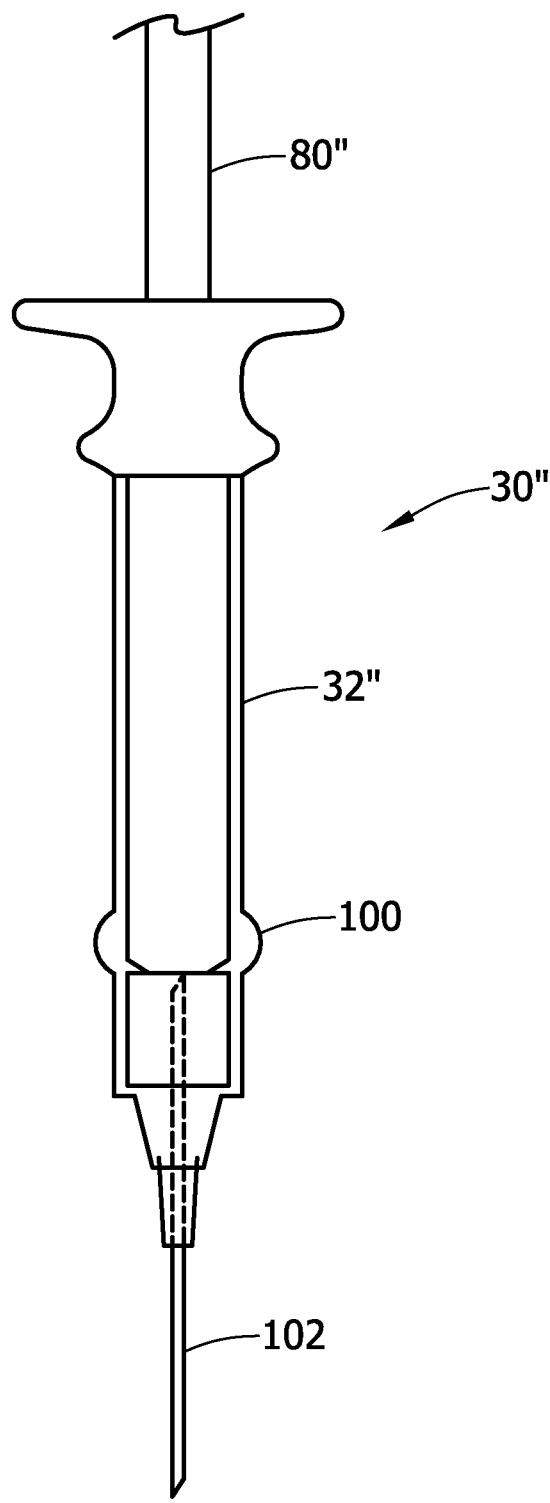
FIG. 5 is a side elevation a syringe assembly of a fifth embodiment of the present invention.

In a fifth embodiment illustrated in FIG. 5, a syringe assembly 30'' includes a polished or convex annular ring 100 surrounding an exterior wall of the barrel 32''. This convex ring 100 magnifies the contents of the barrel 32''. Thus, a user can more readily identify aspirate or flashback flowing backward through the delivery needle 102 and into the syringe assembly 30''. As other aspects of this embodiment are generally similar to those described above, they will not be described.

Figure 6:
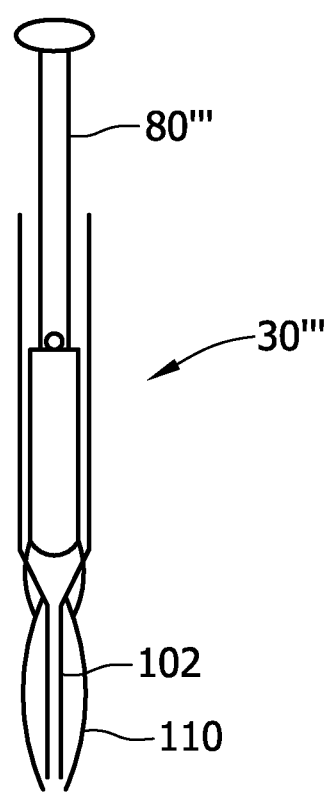
FIG. 6 is a side elevation of a syringe assembly of a sixth embodiment of the present invention.

FIG. 6 illustrates a sixth embodiment of a syringe assembly 30''' of the present invention. In some instances patients become anxious upon seeing a needle of the syringe. To prevent the patient from seeing the needle 102, an elastomeric sleeve 110 is fastened over the delivery needle of the syringe assembly 30'''. When the syringe assembly 30''' is armed, the plunger rod 80''' forces the delivery needle 102 through the elastomeric sheath 110, exposing the needle for use. Other aspects of this embodiment are similar to those described above and will not be described.

Figure 7:
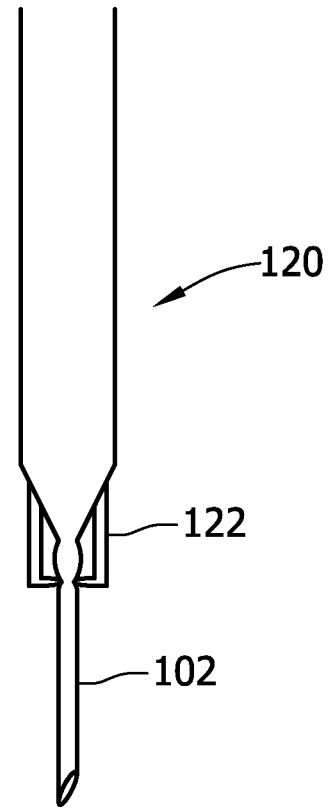
FIGS. 7-10, 11a-d, 12, and 13 are side elevations of various alternative embodiments of the present invention.

Various portions of the syringe assembly may be made reusable to minimize waste. By selectively choosing the portions of the syringe assembly that are disposable, the need for sterilization may be minimized or eliminated. For example, in one embodiment illustrated in FIG. 7, a seventh embodiment of a syringe assembly, generally designated by 120, includes a quick release coupling 122 that holds the needle 102 in place. When a user is finished using the syringe assembly 120, the coupling 122 is disconnected so the needle 102 can be discarded. In some alternate embodiments having the needle and cartridge joined as a sub-assembly, releasing the coupling 122 can operate to eject the entire sub-assembly. It is envisioned that an element could be included on a sharps container for disconnecting the coupling 122.

Figure 8:
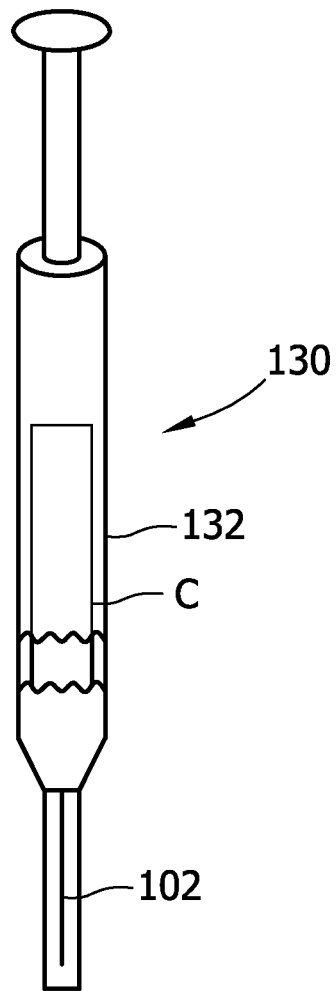
Figure 9:
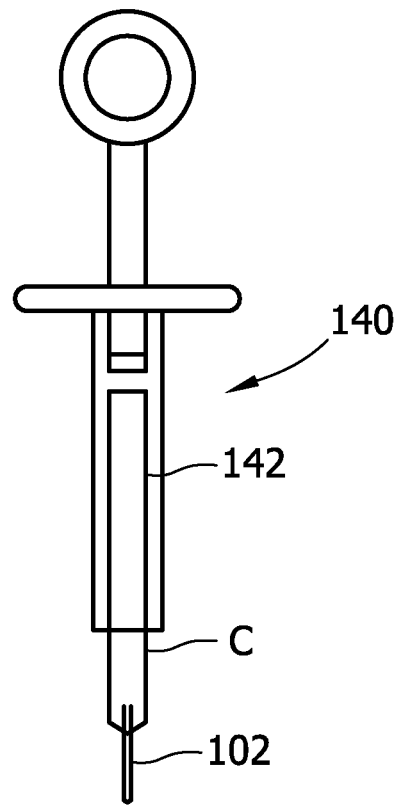
Figure 10:
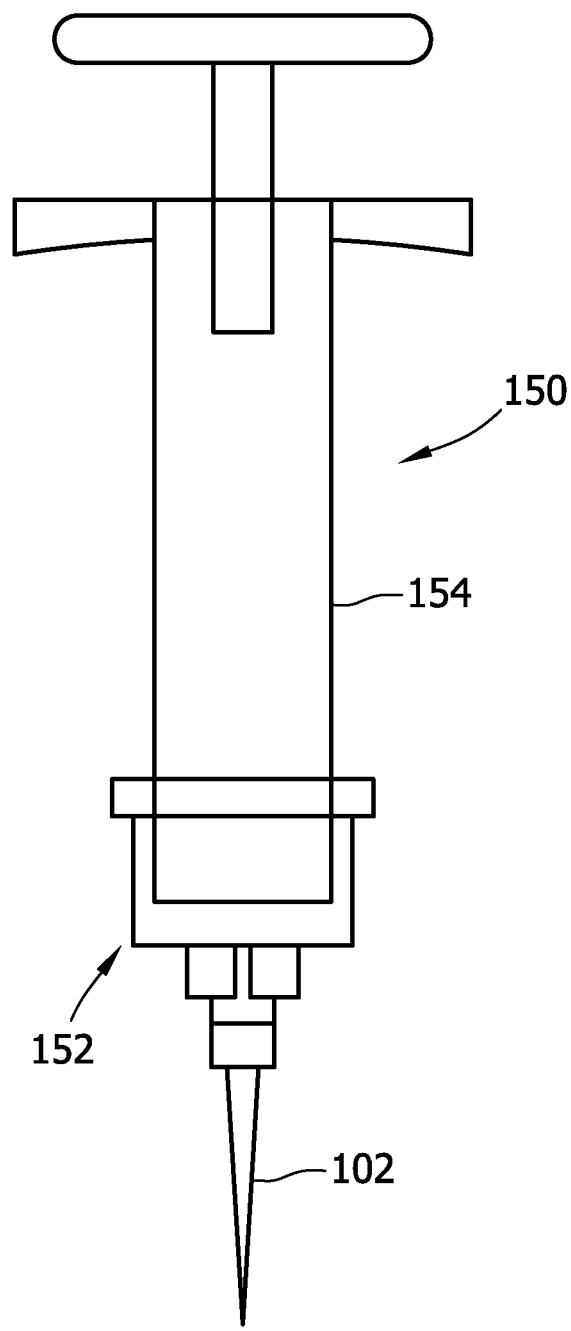
Figure 11A:
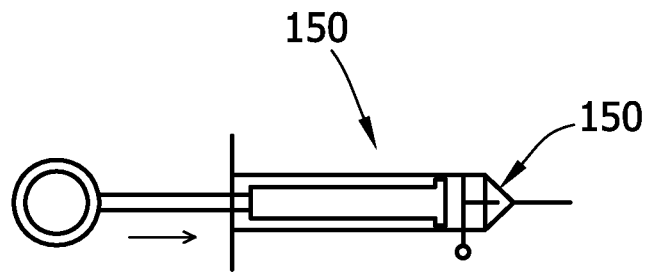
Figure 11B:
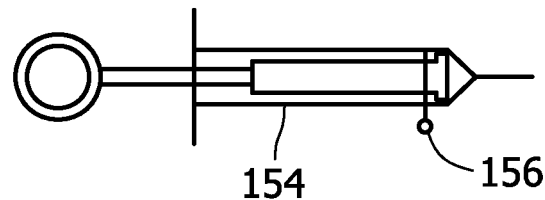
Figure 11C:
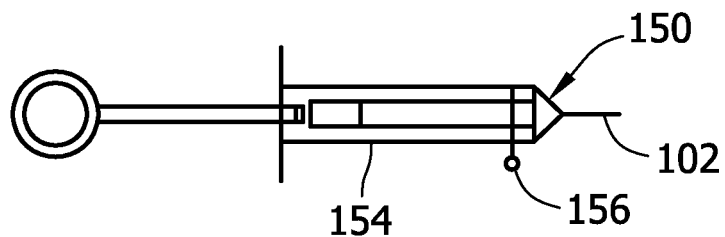
Figure 11D:
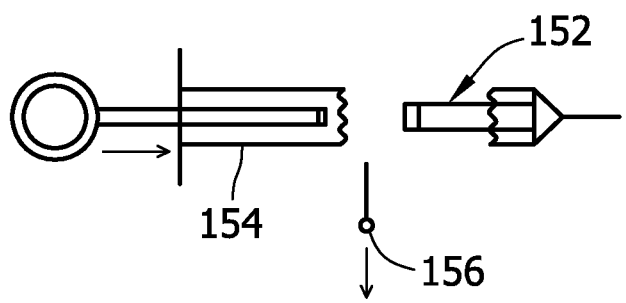
Figure 12:
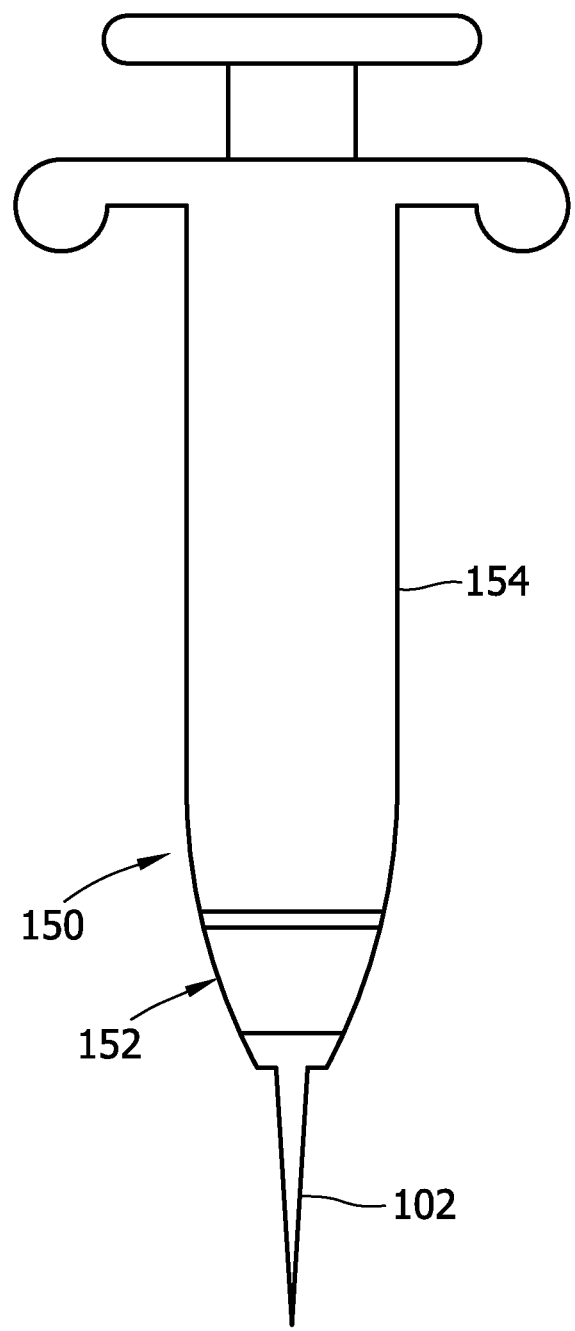

In another embodiment of a syringe assembly, generally designated by 130 in FIG. 8, a barrel 132 separates so the needle 102 and cartridge C can be discarded. Likewise, in another embodiment of a syringe assembly, generally designated by 140 in FIG. 9, a plunger rod 142 separates to release the needle and cartridge C. In an embodiment of a syringe assembly, generally designated by 150 in FIG. 10, a sub-assembly, generally designated by 152, comprising the needle and a cartridge (not shown) separates from the barrel 154 so the needle 102 and cartridge C can be discarded. The sub-assembly 152 may be fastened to the barrel 154 in any conventional way, such as by a press fit connection as shown in FIG. 10. Alternatively, the sub-assembly 152 may be fastened to the barrel 154 by a pin 156 that can be removed as shown in FIGS. 11a-d. In still another embodiment shown in FIG. 12, the sub-assembly 152 is threadably connected to the barrel 154 of the syringe assembly 150. As will be appreciated by those skilled in the art, the disposable portion need not only include a distal portion of a barrel, but may also include a longer portion of the barrel 160 as in a syringe assembly, generally designated by 162 in FIG. 13. In another embodiment (not shown), a distal end of the barrel may include flexible leaves (similar to the leaves described below with respect to FIG. 18) so the sub-assembly can be ejected through the barrel by pushing the plunger rod. It is envisioned that a spring could be incorporated in the syringe assembly to aid ejection of the sub-assembly.

Figure 13:
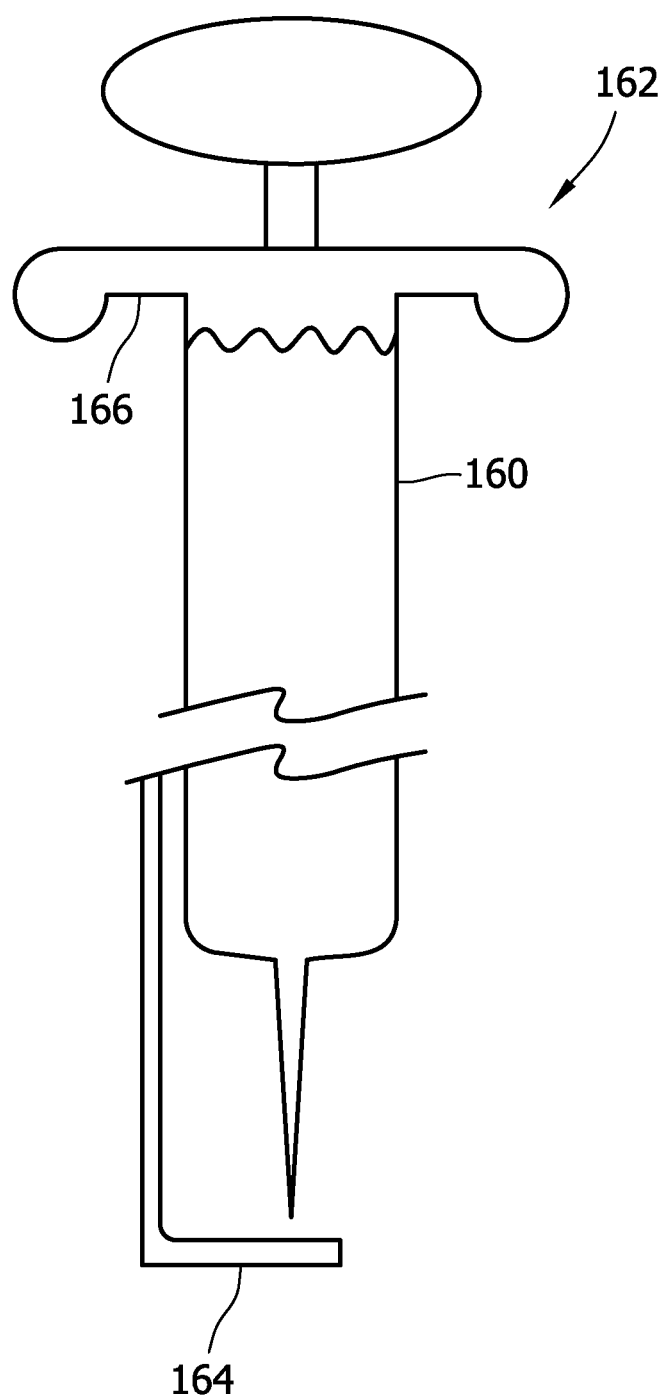

The syringe assembly designated by 162 in FIG. 13 also includes other features of interest. In particular, the syringe assembly 162 includes a needle guard 164 extending from the barrel 160 to a position beyond the needle 102. It is envisioned that this guard 164 can be folded so its distal end lies adjacent a finger flange 166 when the assembly is ready to use. When injection is complete, the guard 164 could be released permitting it to return to the unfolded configuration in which it could provide protection against inadvertent needle sticks. Further, the guard 164 may be made in a contrasting color so that flashback or aspirate is more apparent. The contrasting colors may include phosphorescent coloring. Alternatively, the barrel may be light transmitting or include back lighting or front lighting to further improve visibility of aspirate or flashback.

Figure 14A:
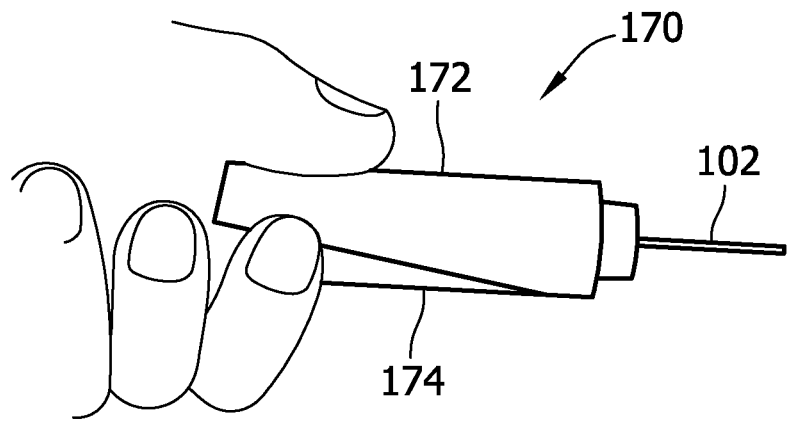
FIG. 14a-c are perspectives of a syringe assembly having a needle guard.
Figure 14B:
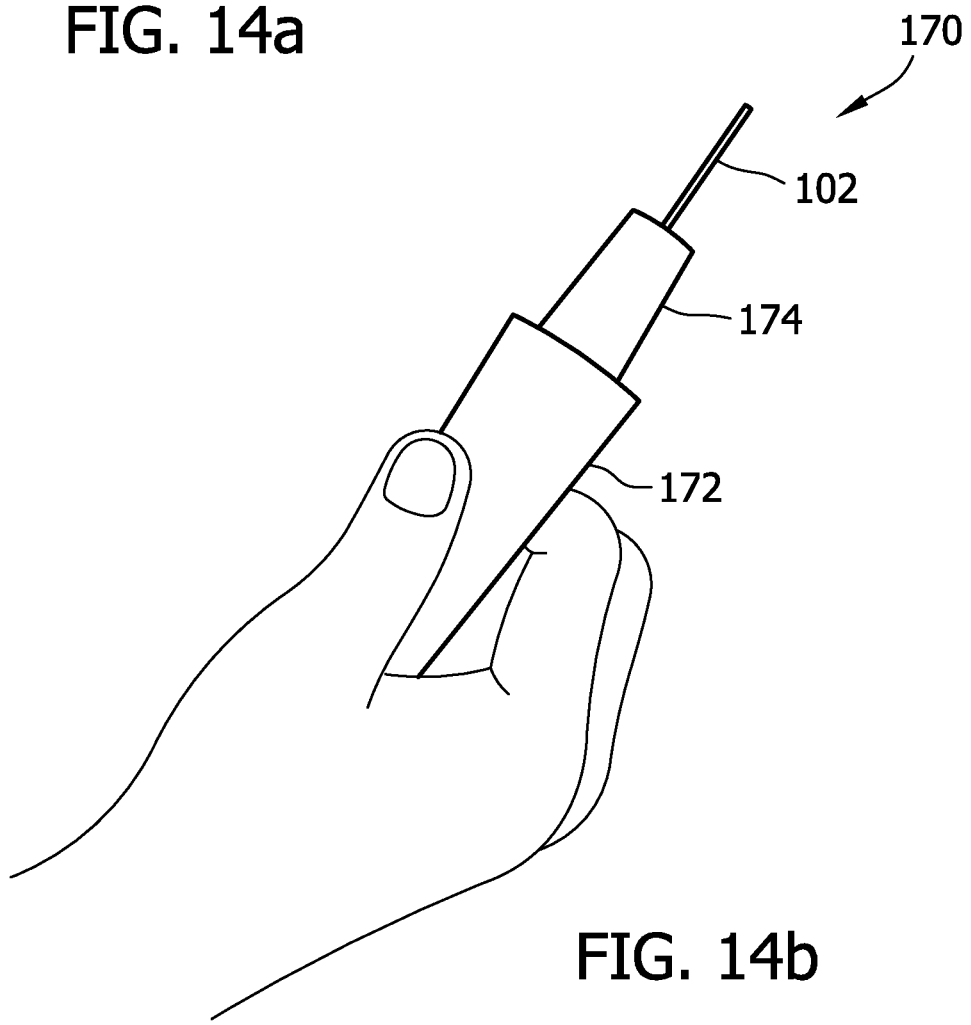
Figure 14C:
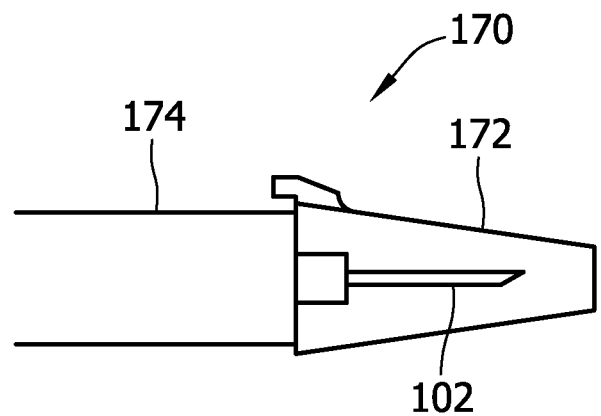

FIGS. 14a-c illustrate an alternate embodiment of a syringe assembly, generally designated by 170, having a needle guard 172. Before use, the guard 172 is pulled proximally onto the syringe body 174. After use, the guard is pushed distally over the needle 102 as shown in FIG. 14c. As will be appreciated by those skilled in the art, needle guards aid in preventing inadvertent needle stabs.

Figure 16:
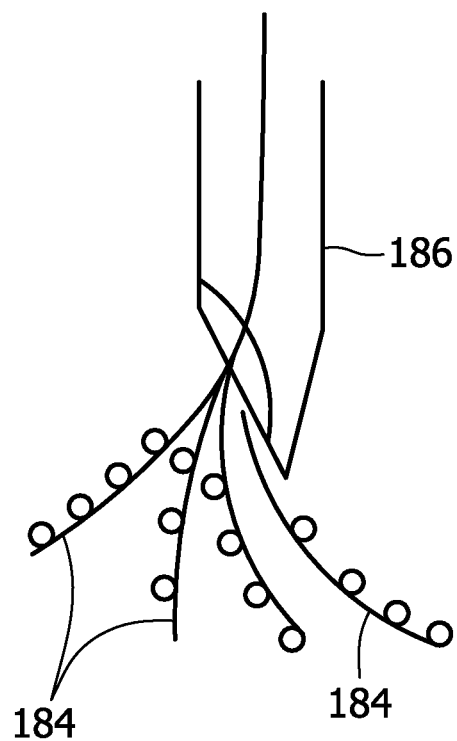
FIG. 16 is a side elevation of a needle of an alternate embodiment of the present invention.
Figure 15:
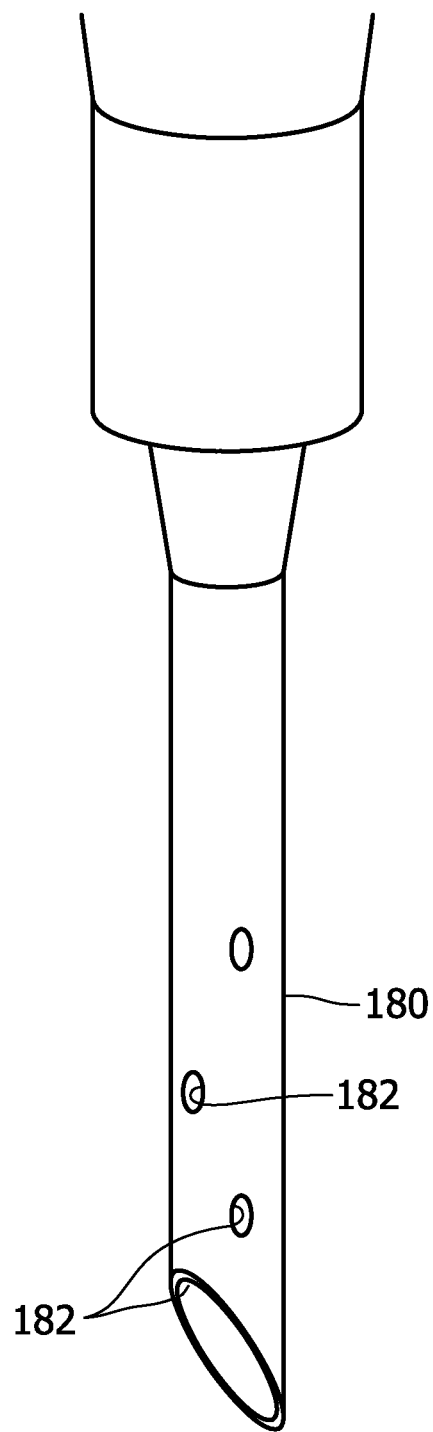
FIG. 15 is a side elevation of a needle of one embodiment of the present invention.

In some dental operations, anesthetic is desired over a broad area of tissue. Pulling a needle out of tissue and repositioning it to inject anesthetic in a different area can be painful for the patient. Thus, there is a need for a dental syringe that is capable of spreading anesthetic from a single injection site. FIG. 15 illustrates an embodiment of a delivery needle 180 having multiple openings 182 along its length for spreading the anesthetic over a broader area of tissue. FIG. 16 illustrates yet another embodiment, in which thin fibers 184 are extended from the needle 186. The fibers 184 fan out and cause multiple punctures in the patient's tissue that may be flooded with anesthetic so the tissue receives anesthetic over a broad area. It is envisioned that the fibers 184 may be made more flexible than the delivery needle but have sufficient rigidity to allow them to penetrate the tissue as they extend out of the needle 186. In one embodiment, the fibers are solid rather than hollow, leaving puncture holes that can be flooded with anesthetic. It is believed that multiple injection sites could reduce discomfort by reducing forces applied to each site.

Figure 17:
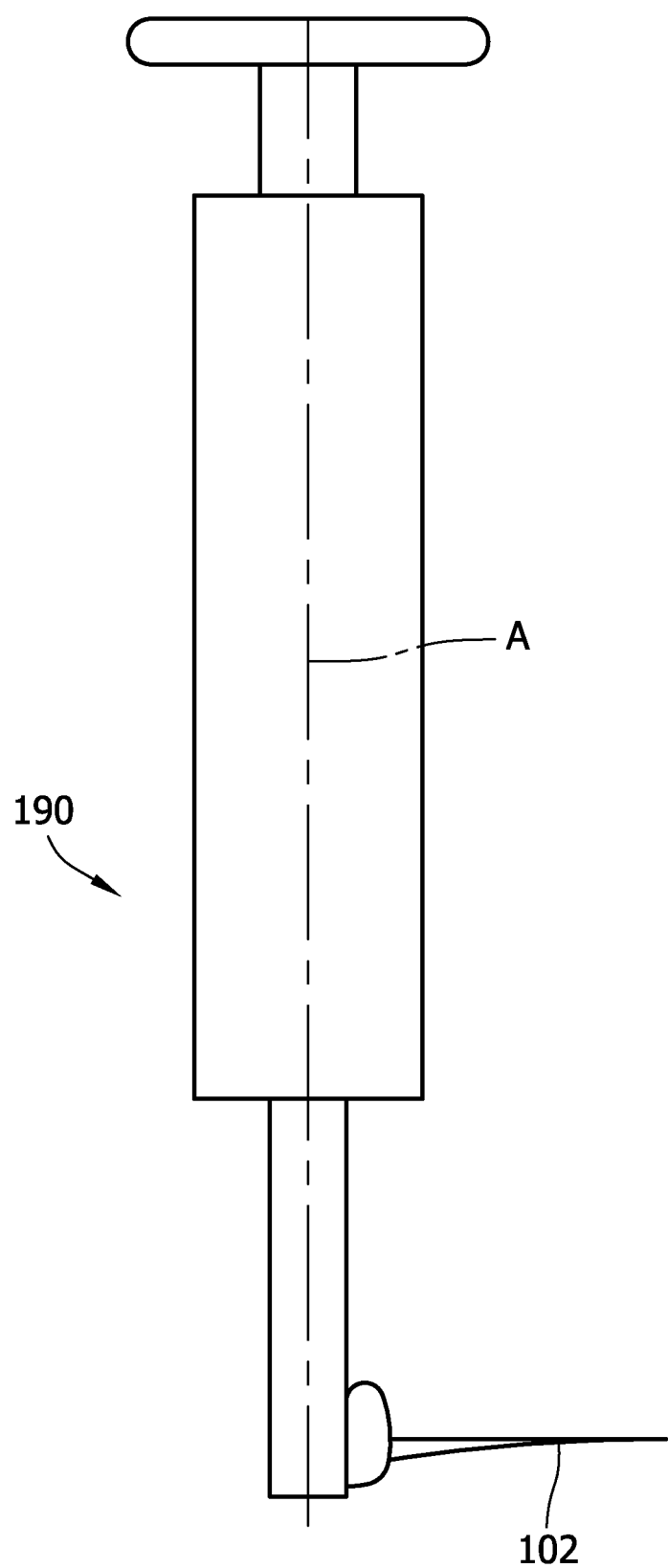
FIG. 17 is a side elevation of a syringe assembly of another embodiment of the present invention.

As previously mentioned, some patients become agitated or anxious at the sight of a conventional aspirating syringe. In order to provide less intimidating form factors for syringe assemblies, various modifications can be made to their configurations and appearance. For example, the syringe assembly may be colored to blend with the user's gloves, thereby camouflaging the syringe assembly. Alternately, the delivery needle 102 may be configured to extend perpendicular to a primary axis A of the syringe assembly, generally designated by 190, as illustrated in FIG. 17. This form factor may mimic other dental tools, such as water syringes, to reduce a likelihood recognition by the patient.

Figure 18:
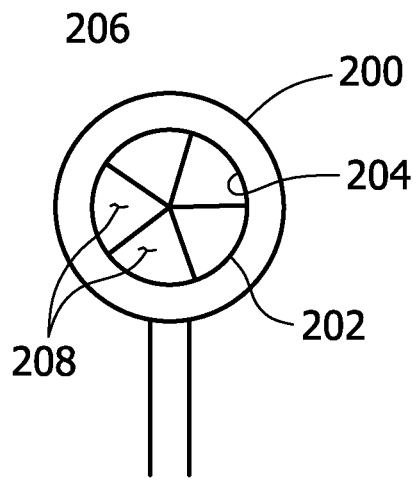
FIG. 18 is a side elevation of a thumb ring of a syringe assembly of another embodiment of the present invention.

FIG. 18 illustrates an automatically sizing thumb ring 200 that may be incorporated in any of the embodiments described above. The thumb ring 200 includes an elastomeric panel 202 extending across its central opening 204. The panel 202 includes spaced radially extending slots 206, forming leaves 208 in the panel that are separately deformed when the user's thumb is inserted in the ring 200. As will be appreciated by those skilled in the art, the leaves 208 of the panel 202 are biased toward the thumb, providing an appropriate fit. Alternatively, the thumb ring may be comprised of two halves ratcheted together. In one embodiment, ratchet teeth on one half operatively engage ratchet teeth on the other half of the thumb ring. The two halves may be compressed toward one another and locked via the ratchets to reduce the internal size of the thumb ring. Similarly, the two halves may be expanded and locked via ratchets to increase the internal size of the thumb ring. This automatically sizing thumb ring permits users having smaller and weaker hands to use the syringe. The ratchet locking mechanism of the thumb ring allows the user to both advance and retract the plunger rod without repositioning the hand.

Figure 19:
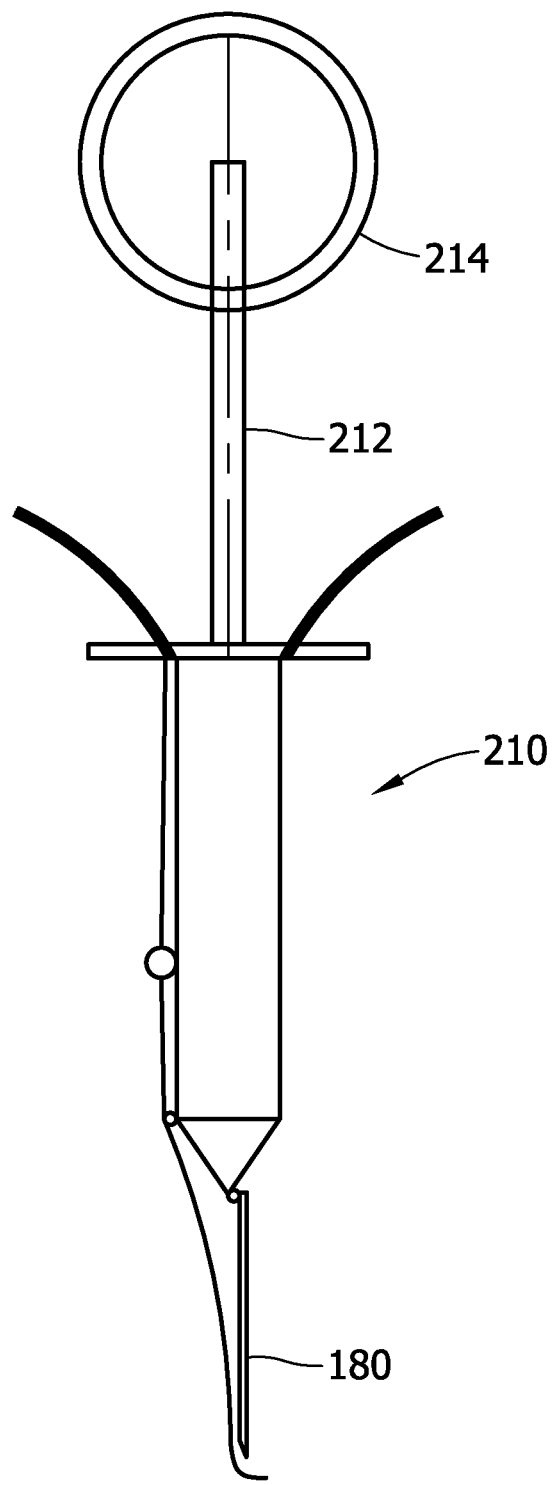
FIG. 19 is a side elevation of a syringe assembly of yet another embodiment of the present invention.

An alternate embodiment of a syringe assembly, designated generally by 210 in FIG. 19, includes a plunger rod 212 having an elastomeric foam ball 214 in place of the conventional thumb ring. Elastomeric ball 214 may have any size and shape to conform to a user's hand, such as round or oval. It is believed such a configuration would provide a less intimidating form factor and provide a more universal fit for users. In an alternate embodiment, the elastomeric foam ball and plunger rod are replaced with an elastomeric hollow bulb that is squeezed to pressurize the anesthetic so that it is ejected from the delivery needle 102. It is believed this alternate embodiment would provide a smooth and continuous flow of anesthetic to the patient because the bulb would dampen pressure changes, as well as provide a less intimidating form factor and a more universal fit for users.

Figure 20:
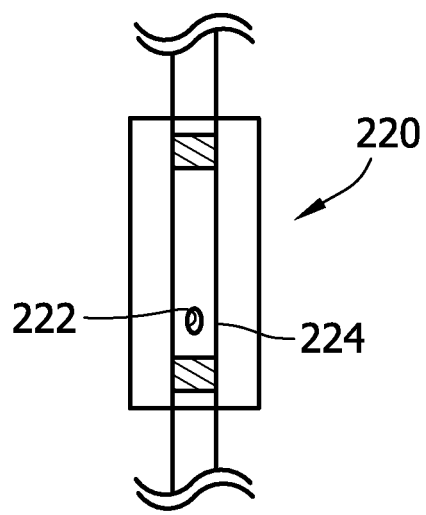
FIG. 20 is a schematic elevation of a portion of a syringe assembly of the present invention.

FIG. 20 shows an accumulator element, generally designated by 220, that could be incorporated in different locations of a syringe assembly. The element 220 is used along a hollow passage to minimize pressure changes. A hole 222 is provided along the passage and an elastomeric balloon or bulb 224 is positioned around the area of the passage having the hole. The balloon or bulb 224 provides an elastomeric fluid accumulator. As anesthetic is delivered through the passage, the accumulator expands and contracts to absorb and release fluid as pressure varies in the passage. Thus, anesthetic may be delivered at a more constant pressure, thereby potentially reducing discomfort of the patient. It is envisioned that a damper could be formed along the plunger rod to accomplish a similar result.

Having described the invention in detail, it will be apparent that modifications and variations are possible without departing from the scope of the invention defined in the appended claims.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A syringe assembly for dispensing medicine from a cartridge having a diaphragm and a piston opposite the diaphragm, said assembly comprising:
    a barrel having a hollow interior, an open proximal end extending into the hollow interior, a closed distal end opposite the proximal end, and an outlet provided in the closed distal end and adapted for fluid communication with a delivery needle for delivering medicine to tissue of a subject; and
    a cartridge receiver slidably receivable in the hollow interior of the barrel, the cartridge receiver including an interior space sized and shaped for receiving the cartridge, an access needle extending into the interior space of the cartridge receiver for puncturing the diaphragm of the cartridge received in the interior space to access medicine therein, the access needle directing fluid to the barrel outlet when the diaphragm is pierced by the access needle, and a plunger rod movable into the interior space of the cartridge receiver for engaging the piston of the cartridge received in the receiver to selectively force medicine in the cartridge through the access needle,
    wherein the cartridge receiver includes a cartridge receiver thumb ring for manipulating the assembly when dispensing medicine from the cartridge, the cartridge receiver thumb ring extending proximally from the hollow interior along a plane parallel to a longitudinal axis of the syringe assembly, and
    wherein the plunger rod includes a plunger rod thumb ring for manipulating the assembly when dispensing medicine from the cartridge, the plunger rod thumb ring extending proximally from the plunger rod along a plane parallel to a longitudinal axis of the syringe assembly, said cartridge receiver thumb ring and said plunger rod thumb ring being concentrically aligned to define a common through-hole when the cartridge is in the interim space of the cartridge receiver, the access needle is fully inserted in the diaphragm of the cartridge, and the plunger rod is engaging the piston of the cartridge.

2. A syringe assembly as set forth in claim 1, wherein the cartridge receiver includes an opening for loading the cartridge into the interior space of the cartridge receiver and a cover for selectively covering the opening to retain the cartridge in the interior space.

3. A syringe assembly as set forth in claim 2, wherein the cover includes the access needle.

4. A syringe assembly as set forth in claim 3, wherein the cartridge receiver further includes a seal for engaging the barrel to seal an interface between the cartridge receiver and the barrel.

5. A syringe assembly as set forth in claim 1, wherein a plurality of leaves extend into the thumb ring to engage a thumb inserted in the ring.

6. A syringe assembly as set forth in claim 1, wherein the cartridge receiver interior space is sized and shaped for receiving a plurality of cartridges, the cartridge receiver has a plurality of access needles corresponding to the plurality of cartridges so each of the access needles punctures one of the cartridge diaphragms, and the cartridge receiver has a plurality of plunger rods corresponding to the plurality of cartridges so each of the plunger rods engages one of the cartridge pistons to selectively force medicine from each of the plurality of cartridges through the corresponding access needle.

7. A syringe assembly as set forth in claim 6, wherein the plunger rods are joined by a common thumb ring so the plunger rods move simultaneously.

8. A syringe assembly as set forth in claim 1, wherein the barrel is separable, allowing the barrel to be discarded separately from the cartridge and needle.

9. A syringe assembly as set forth in claim 1, further comprising a delivery needle downstream from the access needle for delivering medicine to tissue of a subject.

10. A syringe assembly as set forth in claim 9, further comprising a retractable needle guard selectively retractable from an extended position in which the guard limits access to the delivery needle to prevent inadvertent sticks to a retracted position in which the guard permits access to the delivery needle to permit insertion of the delivery needle into tissue of the subject.

11. A syringe assembly as set forth in claim 9, wherein the needle extends perpendicular to the barrel.

12. A syringe assembly as set forth in claim 9, wherein the delivery needle includes a plurality of openings for delivering medicine to tissue of a subject.

13. A syringe assembly as set forth in claim 1, wherein the barrel includes an annular lens surrounding the barrel to magnify contents of the barrel.

14. A syringe assembly as set forth in claim 1, further comprising an elastomeric fluid accumulator downstream from the cartridge absorbing and releasing fluid as pressure varies in the accumulator to provide the medicine at an invariant pressure.

15. The syringe assembly as set forth in claim 1, further comprising an elastomeric sleeve positioned over the delivery needle.

* * * * *